United States Patent
Akutagawa et al.

(10) Patent No.: US 9,233,227 B2
(45) Date of Patent: Jan. 12, 2016

(54) OPERATING MEMBER

(71) Applicant: TERUMO KABUSHIKI KAISHA, Tokyo (JP)

(72) Inventors: Ayaka Akutagawa, Kanagawa (JP); Yuichi Tada, Kanagawa (JP); Tomonori Hatta, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/397,409

(22) PCT Filed: Apr. 22, 2013

(86) PCT No.: PCT/JP2013/061794
§ 371 (c)(1),
(2) Date: Oct. 27, 2014

(87) PCT Pub. No.: WO2013/161764
PCT Pub. Date: Oct. 31, 2013

(65) Prior Publication Data
US 2015/0080792 A1 Mar. 19, 2015

(30) Foreign Application Priority Data
Apr. 27, 2012 (JP) ................................. 2012-104094

(51) Int. Cl.
*A61M 25/01* (2006.01)
*A61B 19/00* (2006.01)
*A61B 17/00* (2006.01)

(52) U.S. Cl.
CPC ............ *A61M 25/0147* (2013.01); *A61B 19/00* (2013.01); *A61M 25/0136* (2013.01); *A61B 2017/00323* (2013.01)

(58) Field of Classification Search
CPC ..................... A61M 25/0147; A61M 25/0136; A61M 25/0133; A61M 2025/015; A61B 19/00; A61B 2017/00323; A61B 1/0051; A61B 1/0057; A61B 1/0052; A61B 2017/00318
USPC .................. 604/528, 95.04; 600/139–142
See application file for complete search history.

(56) References Cited

U.S. PATENT DOCUMENTS

RE34,502 E      1/1994   Webster, Jr.
5,891,088 A *   4/1999   Thompson ........ A61M 25/0136
                                                    604/524

(Continued)

FOREIGN PATENT DOCUMENTS

JP    2000279528 A    10/2000
JP    2000312720 A    11/2000

(Continued)

OTHER PUBLICATIONS

Non-Patent Literature search conducted by STIC (Science and Technical Information Center), dated Sep. 1, 2015.*

(Continued)

*Primary Examiner* — Kami A Bosworth
*Assistant Examiner* — Hamza Darb

(57) ABSTRACT

An object of the present invention is to provide an operating member with which curving operation of a catheter distal part can be easily carried out without moving a comparatively-large member. An operating member has a rotational operation part (10) that is fixed to an elongated body (100) for medical use and rotates the elongated body for medical use about the axis, pull wires (20) fixed to the elongated body for medical use, and a pull operation part (30) that is connected to the pull wires and curves at least part of the elongated body for medical use in a direction intersecting the axial direction by pulling the pull wire. The operating member further has a support part (40) that is provided rotatably about the axis of the elongated body for medical use and supports the pull operation part in such a state that the pull action of the pull operation part is possible, joining parts (50) that join the rotational operation part to the support part and rotate the support part and the pull operation part about the axis of the elongated body for medical use in association with the rotation of the rotational operation part, and a grip part (60) that is restricted in movement in the axial direction by being disposed between the rotational operation part and the support part and is provided pivotally independently of the rotational operation part and the support part.

8 Claims, 12 Drawing Sheets

(56) References Cited

U.S. PATENT DOCUMENTS 6,183,435 B1    2/2001    Bumbalough et al.
6,203,507 B1    3/2001    Wadsworth et al.

FOREIGN PATENT DOCUMENTS

| | | |
|---|---|---|
| JP | 200893385 A | 4/2008 |
| JP | 2010094484 A | 4/2010 |
| WO | 2013161764 A1 | 10/2013 |

OTHER PUBLICATIONS

Patent search conducted by STIC (Science and Technical Information Center), dated Sep. 1, 2015.*
Written Opinion (in Chinese language) issued on Aug. 6, 2013 by the International Searching Authority ("ISA"), 3 pages.
Written Opinion (in Chinese language) issued on Jul. 23, 2013 by the International Searching Authority ("ISA"), 3 pages.

* cited by examiner

OPERATING MEMBER

CROSS REFERENCE TO RELATED APPLICATIONS

This application is based on International Application No. PCT/JP2013/061794, filed on Apr. 22, 2013, which claims priority to Japanese National Application No. 2012-104094, filed on Apr. 27, 2012. the entire contents of each and every foregoing application are incorporated herein by reference.

TECHNICAL FIELD

The present invention relates to an operating member of an elongated body for medical use.

BACKGROUND ART

In recent years, in the medical field, various treatments and tests are performed by using a medical instrument that is called a catheter and has a shape of an elongated, soft hollow tube. Examples of treatment methods include a method in which a medication is directly administered to an affected area by utilizing the elongated shape of a catheter, a method in which a stenosed part in a body cavity is pushed to be dilated by using a catheter having a distal end to which a balloon dilated by pressurizing is attached, a method in which an affected area is scraped off by using a catheter having a distal part to which a cutter is attached, and a method in which, conversely, an aneurysm, bleeding site, or feeding vessel is stuffed to be closed by using a catheter. Furthermore, there is e.g. a treatment method in which a stent having a shape of a tube whose side surface has a mesh shape is buried and indwelled in a body cavity by using a catheter in order to keep a stenosed part in a biological lumen at an opened state. Moreover, an excess liquid for the inside of a body is often sucked via a catheter.

To perform the above-described procedures, the catheter distal part needs to be made to reach the target site. However, biological lumens such as tracheae, digestive tracts, and blood vessels are intricate with bifurcations and therefore it is difficult to make the catheter distal part reach the target site. Therefore, it is important to control the curving direction of the catheter distal part.

As a technique relating to this, a catheter having a housing provided with a piston chamber at the distal part is described in Patent Document 1 to be shown below. According to this technique, a piston provided in the piton chamber moves in the length direction relative to the housing to thereby curve the catheter distal part. Furthermore, in Patent Document 2 to be shown below, a catheter having a control handle to which a first pull wire anchor and a second pull wire anchor are joined and a thumb control unit to control the movement of this control handle in the length direction is described. According to this technique, the catheter distal part is curved by pressing the thumb control unit to move the control handle in the length direction.

PRIOR ART DOCUMENTS

Patent Documents

Patent Document 1: U.S. Pat. No. 34,502
Patent Document 2: Japanese Patent Laid-open No. 2000-312720

SUMMARY OF INVENTION

Technical Problem

However, in the techniques of Patent Documents 1 and 2, a comparatively-large member such as the piston or control handle needs to be moved in curving the catheter distal part. Therefore, there is a problem that the operability of curving operation of the catheter distal part is low.

The present invention is made in order to solve the above-described problem and an object thereof is to provide an operating member with which curving operation of a catheter distal part can be easily carried out without moving a comparatively-large member.

Technical Solution

An operating member according to the present invention that achieves the above-described object is an operating member for rotating an elongated body for medical use about an axis and curving at least part of the elongated body for medical use in a direction intersecting an axial direction. The operating member has a rotational operation part that is fixed to the elongated body for medical use and rotates the elongated body for medical use about the axis, a pull wire fixed to the elongated body for medical use, and a pull operation part that is connected to the pull wire and curves at least part of the elongated body for medical use in a direction intersecting the axial direction by pulling the pull wire. The operating member further has a support part that is provided rotatably about the axis of the elongated body for medical use and supports the pull operation part in such a state that a pull action of the pull operation part is possible, a joining part that joins the rotational operation part to the support part and rotates the support part and the pull operation part about the axis of the elongated body for medical use in association with rotation of the rotational operation part, and a grip part that is restricted in movement in the axial direction by being disposed between the rotational operation part and the support part and is provided pivotally independently of the rotational operation part and the support part.

Advantageous Effect

With the operating member configured in the above-described manner, curving operation of the catheter distal part is enabled by operating the pull operation part. Thus, the curving operation of the catheter distal part can be easily carried out without moving a comparatively-large member.

MODES FOR CARRYING OUT THE INVENTION

<First Embodiment>

Embodiments of the present invention will be described below with reference to the drawings. The dimension ratio of the drawings is exaggerated to differ from the actual ratio in some cases for convenience of description. Furthermore, in the following description, the side of the hand operation part of the device will be referred to as the "proximal side" and the side inserted into a biological lumen will be referred to as the "distal side."

The configuration of a medical instrument 1 according to a first embodiment of the present invention will be described.

Figure 1:
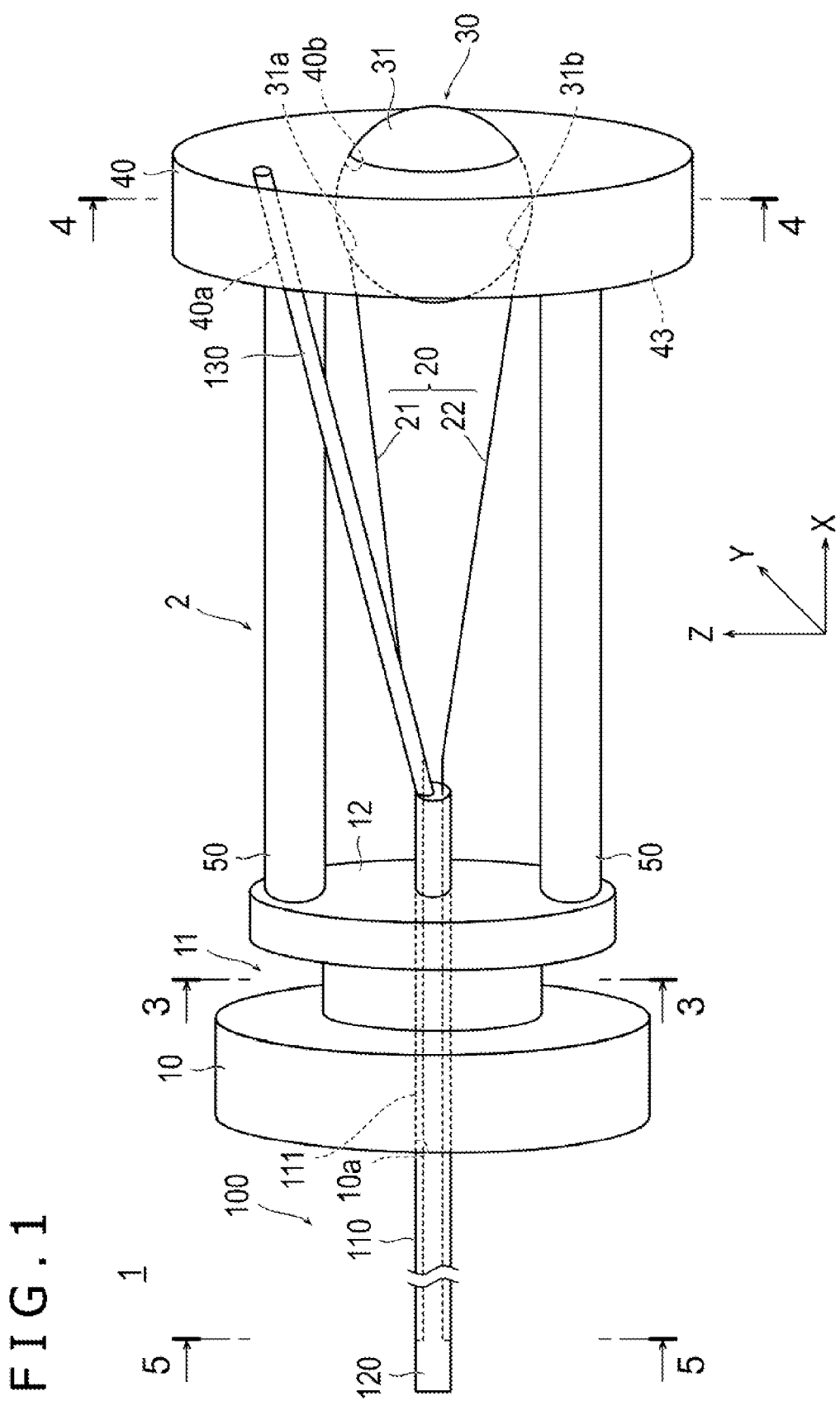
FIG. 1 is a schematic configuration diagram showing a medical instrument according to a first embodiment of the present invention.
Figure 2:
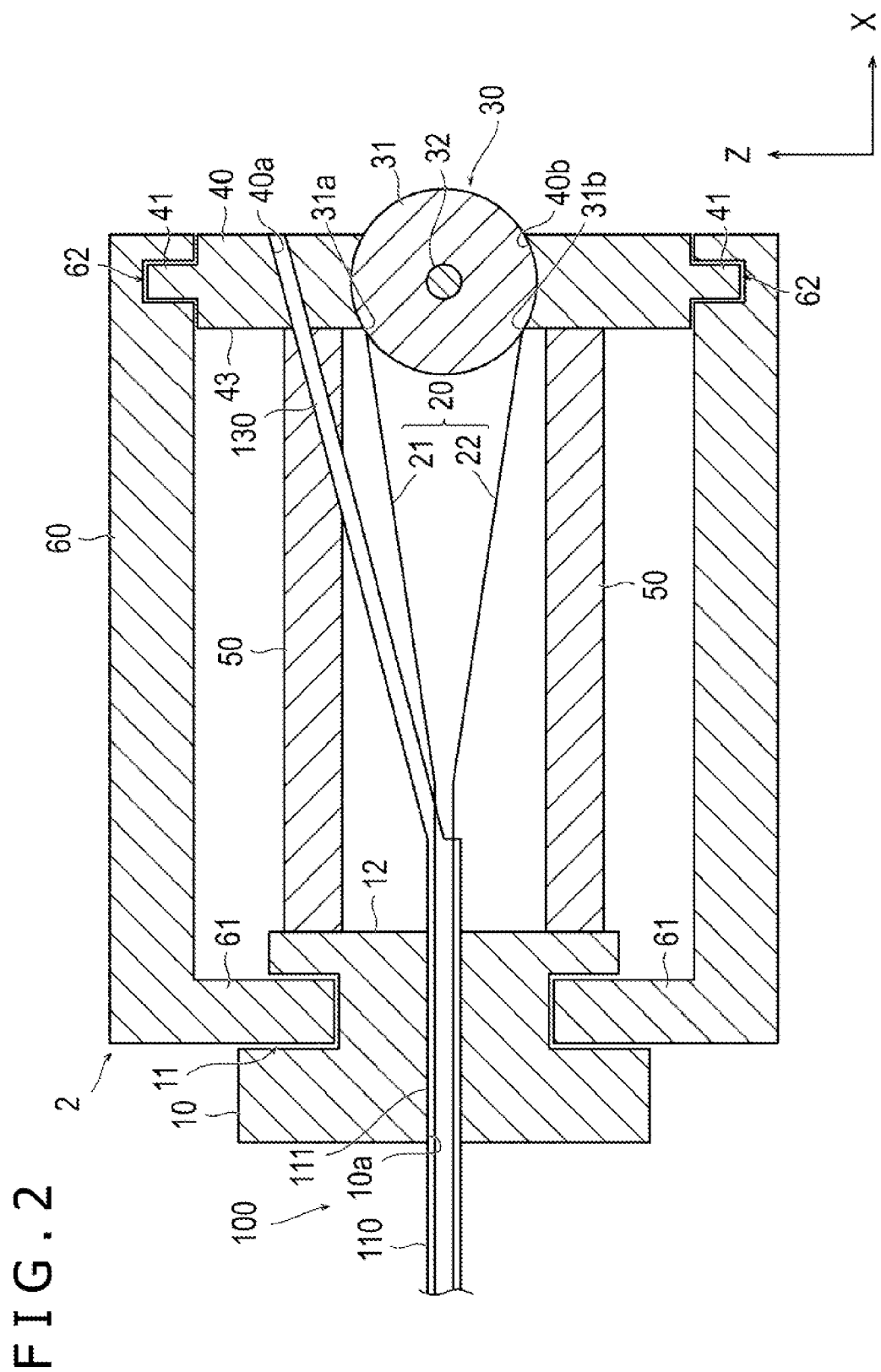
FIG. 2 is a front sectional view showing the medical instrument according to the first embodiment.
Figure 3:
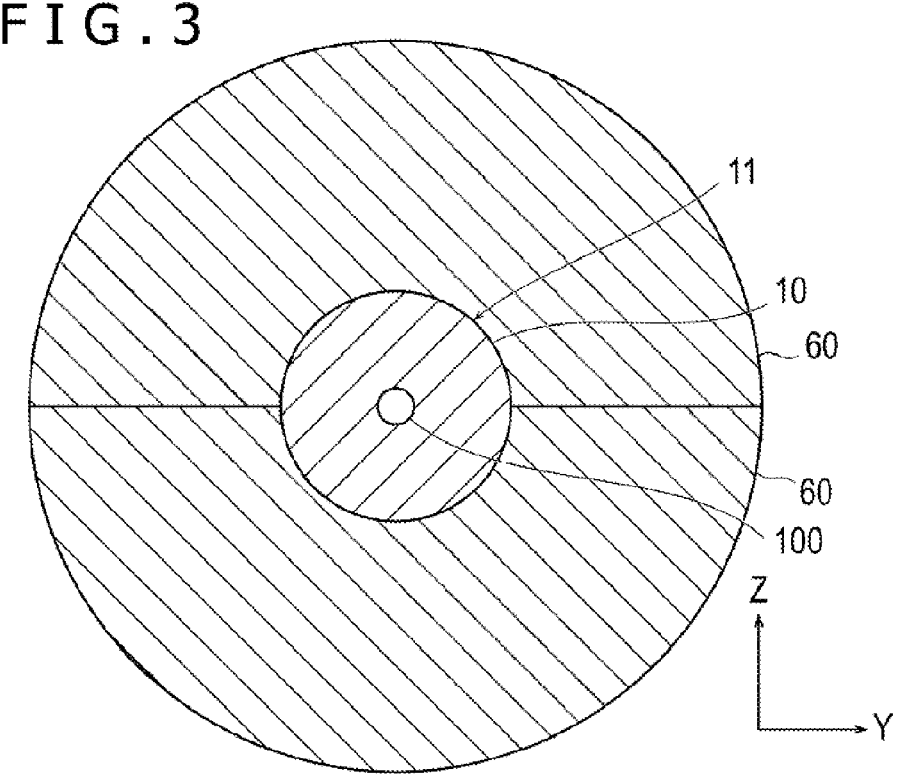
FIG. 3 is a sectional view along line 3-3 in FIG. 1.
Figure 4:
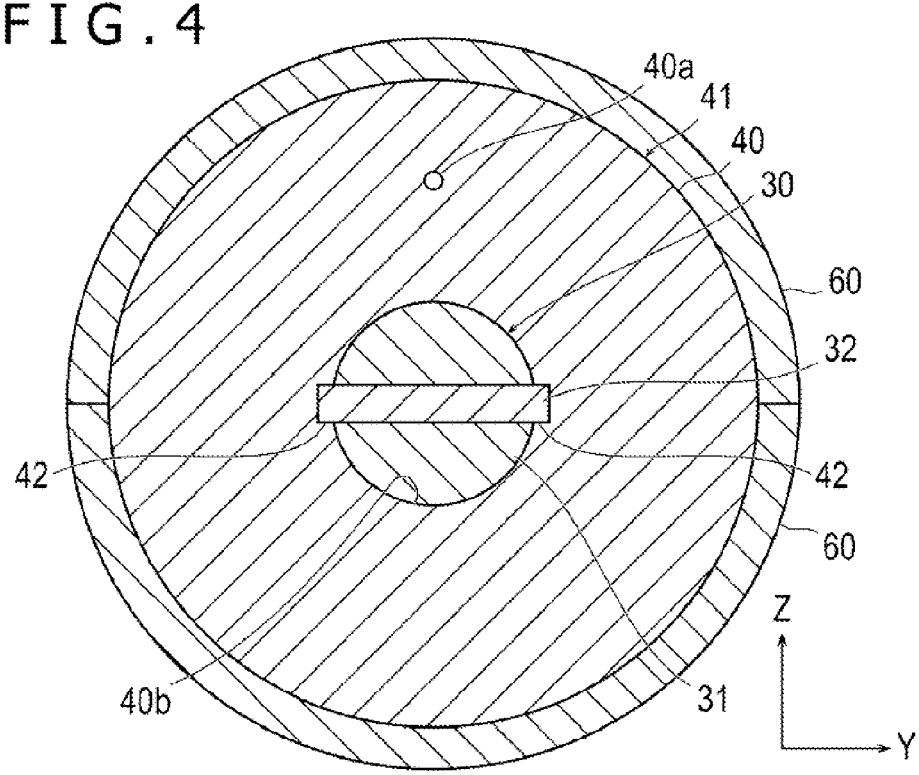
FIG. 4 is a sectional view along line 4-4 in FIG. 1.
Figure 5:
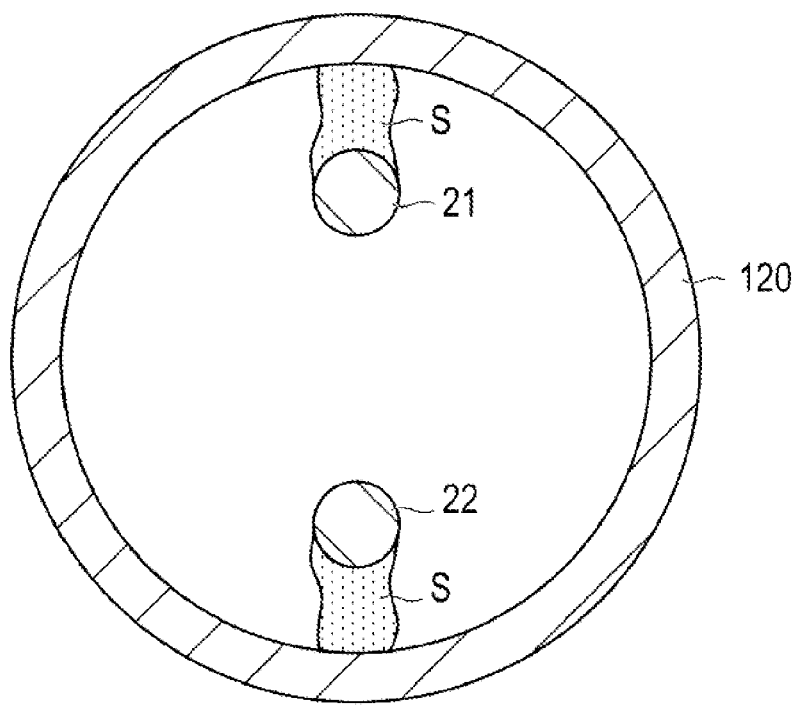
FIG. 5 is a sectional view along line 5-5 in FIG. 1.

FIG. 1 is a schematic configuration diagram showing the medical instrument 1 according to the first embodiment of the present invention. FIG. 2 is a front sectional view showing the medical instrument 1 according to the first embodiment. FIG. 3 is a sectional view along line 3-3 in FIG. 1. FIG. 4 is a sectional view along line 4-4 in FIG. 1. FIG. 5 is a sectional view along line 5-5 in FIG. 1.

As shown in FIGS. 1 to 5, the medical instrument 1 according to the first embodiment of the present invention has a guiding catheter 100 that is an elongated tube having flexibility and an operating member 2 that rotates the guiding catheter 100 about the axis and curves at least part of the guiding catheter 100 in a direction intersecting the axial direction.

After being inserted into a biological lumen, the guiding catheter 100 guides a procedure instrument, such as a guide wire or a balloon catheter, to perform a treatment to an affected area. Examples of the material to form the guiding catheter 100 include the following resins excellent in the biocompatibility: fluorine resins such as ETFE (ethylenetetrafluoroethylene copolymer) and PTFE (polytetrafluoroethylene); and thermoplastic resins such as polyolefins typified by PE (polyethylene) and PP (polypropylene), polyamide, polyester, and polyurethane. The guiding catheter 100 may contain a radiographic contrast material for checking the position in a body. The guiding catheter 100 has a guiding catheter body part 110 (body part), a guiding catheter distal part 120 (distal part), and a working lumen 130.

The guiding catheter body part 110 has an outer circumference 111 fixed to a rotational operation part 10 to be described later.

The guiding catheter distal part 120 is curved in a direction intersecting the axial direction of the guiding catheter 100 by the operating member 2.

The working lumen 130 is so provided as to extend from the proximal side of the guiding catheter body part 110 to a support part 40 to be described later. The working lumen 130 guides the above-described procedure instrument into the guiding catheter 100 after the guiding catheter 100 is inserted into a biological lumen.

The operating member 2 is to rotate the guiding catheter 100 about the axis and curve at least part of the guiding catheter 100 in a direction intersecting the axial direction. The operating member 2 has the following parts: the rotational operation part 10 that is fixed to the guiding catheter 100 and rotates the guiding catheter 100 about the axis; pull wires 20 fixed to the guiding catheter 100; a pull operation part 30 that is connected to the pull wires 20 and curves at least part of the guiding catheter 100 in a direction intersecting the axial direction by pulling the pull wire 20; the support part 40 that is provided rotatably about the axis of the guiding catheter 100 and supports the pull operation part 30 in such a state that the pull action of the pull operation part 30 is possible; joining parts 50 that join the rotational operation part 10 to the support part 40 and rotate the support part 40 and the pull operation part 30 about the axis of the guiding catheter 100 in association with the rotation of the rotational operation part 10; and a grip part 60 that is restricted in movement in the axial direction by being disposed between the rotational operation part 10 and the support part 40 and is provided pivotally independently of the rotational operation part 10 and the support part 40.

The rotational operation part 10 rotates the guiding catheter 100. The rotational operation part 10 is a hollow member having a through-hole 10a along the extension direction of the guiding catheter 100 (hereinafter, referred to as the X-direction) and has a rotational recess 11 and a rotational joining surface 12.

The through-hole 10a is a through-hole into which the guiding catheter 100 is inserted. The guiding catheter 100 is inserted into the through-hole 10a and the through-hole 10a of the rotational operation part 10 is fixed to the outer circumference 111 of the guiding catheter 100. Thus, by rotating the rotational operation part 10 about the X-axis, the guiding catheter 100 rotates about the X-axis in association with the rotation of the rotational operation part 10. The fixing method is not particularly limited, and the through-hole 10a and the outer circumference 111 can be bonded by e.g. an adhesive or soldering.

The rotational recess 11 is provided near the center of the rotational operation part 10 in the X-direction and along the circumference of the axis of the X-direction. The rotational recess 11 pivotally holds grip protrusions 61 of the grip part 60 to be described later.

The rotational joining surface 12 is provided on the proximal side of the rotational operation part 10 and is joined to the joining parts 50. The joining method is not particularly limited, and the rotational joining surface 12 and the joining parts 50 can be bonded by e.g. an adhesive or soldering.

The pull wires 20 curve the guiding catheter distal part 120. The pull wires 20 have a first wire 21 and a second wire 22 fixed at positions opposed to each other in a section of the guiding catheter distal part 120 perpendicular to the axis (section along line 5-5 in FIG. 1) as shown in FIG. 5. The first wire 21 and the second wire 22 are each fixed to the guiding catheter distal part 120 by an adhesive S. The fixing method is not limited to the adhesive. The pull wires 20 have an outer diameter of e.g. about 0.1 mm and are formed of a metal material such as stainless steel, a superelastic material such as nickel titanium, a resin material, or the like. However, the pull wires 20 are not limited thereto.

The pull operation part 30 pulls the pull wire 20 in a direction intersecting the axial direction of the guiding catheter 100. The pull operation part 30 has a main body part 31 and a restricting member 32.

The main body part 31 pulls the pull wire 20 by a rotational action. As shown in FIG. 1, the main body part 31 has a spherical shape and is connected to the first wire 21 and the second wire 22 at connection points 31a and 31b, respectively. The connecting method is not particularly limited, and the main body part 31 and the first and second wires 21 and 22 can be bonded by e.g. an adhesive or soldering.

The restricting member 32 restricts the rotation direction of the main body part 31. As shown in FIG. 4, the restricting member 32 is so provided as to extend along the direction (hereinafter, defined as the Y-direction) perpendicular to each of the X-direction and the direction in which the connection points 31a and 31b are linked to each other (hereinafter, defined as the Z-direction). The restricting member 32 is held by being inserted into support recesses 42 of the support part 40 to be described later. The holding method is not limited thereto. Because the restricting member 32 extends along the Y-direction, the main body part 31 is rotated about the Y-axis. Although the main body part 31 is a sphere, it is not limited thereto and may be a circular disc, dial, or the like.

The support part 40 supports the pull operation part 30 in such a state that the rotational action of the pull operation part 30 is possible. The support part 40 is a hollow member having a through-hole 40a and a support hole 40b and has a support protrusion 41, the support recesses 42, and a support joining surface 43.

The through-hole 40a is a through-hole into which the working lumen 130 is inserted. It is preferable that, as shown in FIG. 4, the through-hole 40a is made at a position offset from the center of the main body part 31 in the rotation direction of the main body part 31 (Z-direction) in order to clearly indicate the rotation direction of the main body part 31. However, the position thereof is not limited thereto.

The support hole 40b is a hole for supporting the pull operation part 30. A groove may be made around the Y-axis in the inner circumferential surface of the support part 40 on the side of the support hole 40b in order to prevent the interference between the pull wires 20 and the support part 40 when the pull operation part 30 is rotated about the Y-axis. This groove may exist on the side of the pull operation part 30.

As shown in FIG. 2, the support protrusion 41 is provided near the center of the support part 40 in the X-direction and along the circumference of the axis of the X-direction. The support protrusion 41 pivotally holds grip recesses 62 of the grip part 60 to be described later. In FIG. 1, the support protrusion 41 is omitted for clearly showing the structure.

As shown in FIG. 4, the support recesses 42 are made at two places in the Y-direction and the restricting member 32 is inserted into each of them to be fixed.

As shown in FIG. 2, the support joining surface 43 is provided on the distal side of the support part 40 and is joined to the joining parts 50.

The joining parts 50 join the rotational operation part 10 to the support part 40 and transmit rotational motion of the rotational operation part 10 to the support part 40. The joining parts 50 are members extending along the X-direction. Two joining parts 50 are provided at positions opposed to each other in a YZ plane between the rotational operation part 10 and the support part 40 and are joined to the rotational joining surface 12 and the support joining surface 43.

The grip part 60 pivotally holds the rotational operation part 10 and the support part 40. The grip part 60 is bisected along the longitudinal direction (X-direction) as shown in FIGS. 3 and 4 and is so provided as to cover the rotational operation part 10 and the support part 40. The grip part 60 has the grip protrusions 61 and the grip recesses 62. In FIG. 1, the grip part 60 is omitted for clearly showing the structure.

As shown in FIG. 2, the grip protrusions 61 are provided on the distal side of the grip part 60 and are held by the rotational recess 11. The width of the grip protrusions 61 in the X-direction is smaller than the width of the rotational recess 11 in the X-direction and the inner diameter of the grip part 60 at the grip protrusions 61 is larger than the outer diameter of the rotational operation part 10 at the rotational recess 11. Therefore, the grip part 60 freely pivots independently of the rotational operation part 10.

As shown in FIG. 2, the grip recesses 62 are made at the proximal side of the grip part 60 and are held by the support protrusion 41. The width of the grip recesses 62 in the X-direction is larger than the width of the support protrusion 41 in the X-direction and the inner diameter of the grip part 60 at the grip recesses 62 is larger than the outer diameter of the support part 40 at the support protrusion 41. Therefore, the grip part 60 freely pivots independently of the support part 40. The length of the grip part 60 in the X-direction is e.g. about 100 mm to 150 mm and the outer diameter thereof is e.g. about 25 mm. However, the size thereof is not limited thereto.

Next, with reference to FIGS. 6 and 7, the operation of the medical instrument 1 according to the first embodiment of the present invention will be described by taking as an example a case in which the medical instrument 1 is applied to a lung cancer biopsy.

First, an operator inserts a bronchoscope from an oral cavity or a nasal cavity. After inserting the bronchoscope, the operator inserts the guiding catheter 100 into the channel of the bronchoscope.

When the guiding catheter distal part 120 reaches a bifurcation of bronchi, the operator rotates the rotational operation part 10 by using e.g. a second finger or a third finger under radioscopy to rotate the guiding catheter 100 in a proper direction while holding the grip part 60. At this time, because the grip part 60 freely pivots independently of the rotational operation part 10, it is possible to rotate the rotational operation part 10 while holding the grip part 60.

Next, the operator rotates the pull operation part 30 about the Y-axis by using e.g. a thumb under radioscopy. The operator thereby pulls the pull wire 20 in a direction intersecting the axial direction of the guiding catheter 100 (X-direction) to curve the guiding catheter distal part 120.

Figure 6:
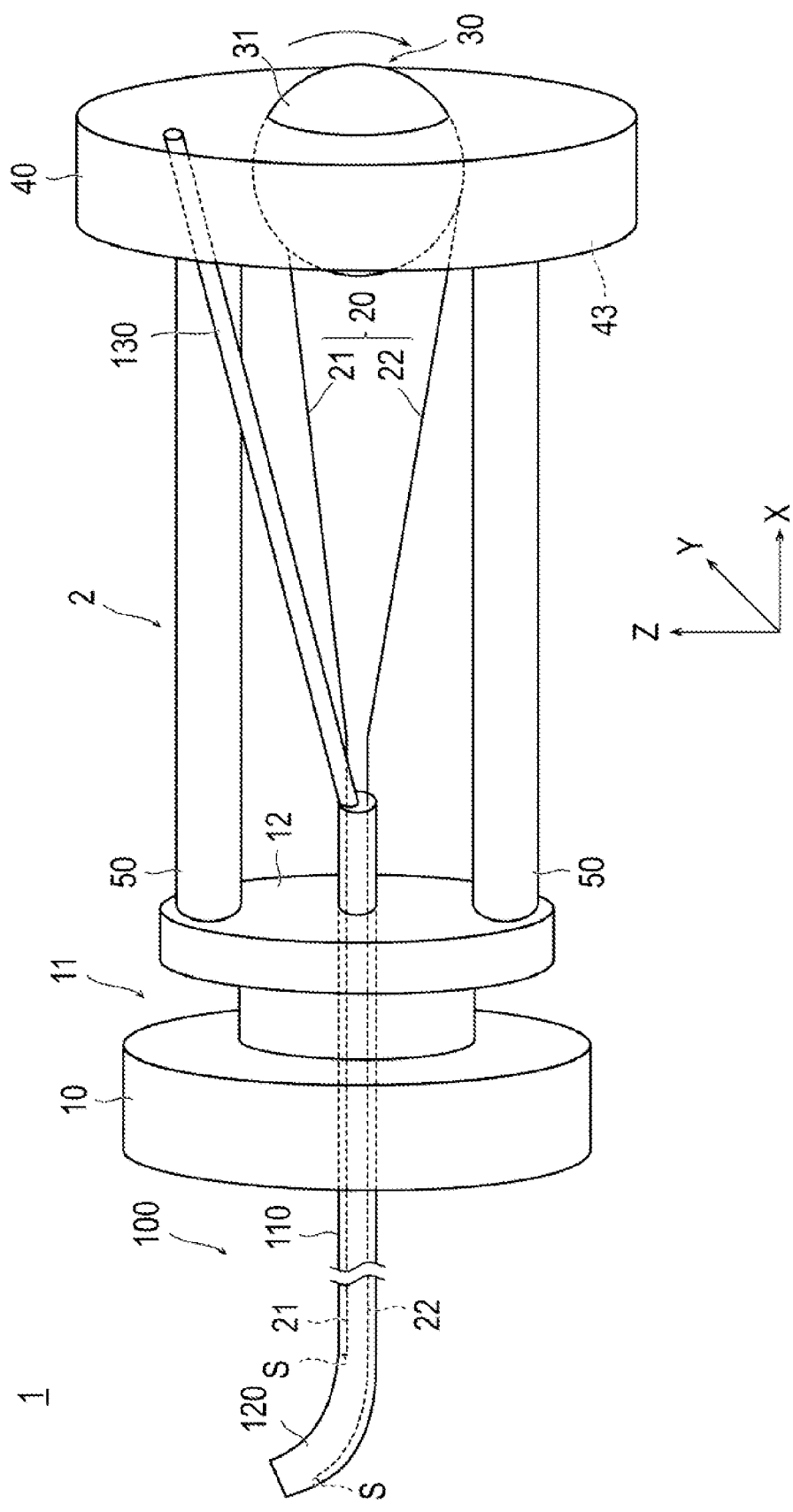
FIG. 6 is a schematic configuration diagram showing the medical instrument when a guiding catheter distal part is curved upward.

Specifically, in the case of curving the guiding catheter distal part 120 in the upward Z-direction in the state of FIG. 1, the operator rotates the pull operation part 30 about the Y-axis from the upper side toward the lower side as shown in FIG. 6 by e.g. a thumb. The first wire 21 is thereby pulled toward the proximal side and thus the guiding catheter distal part 120 is curved upward.

Figure 7:
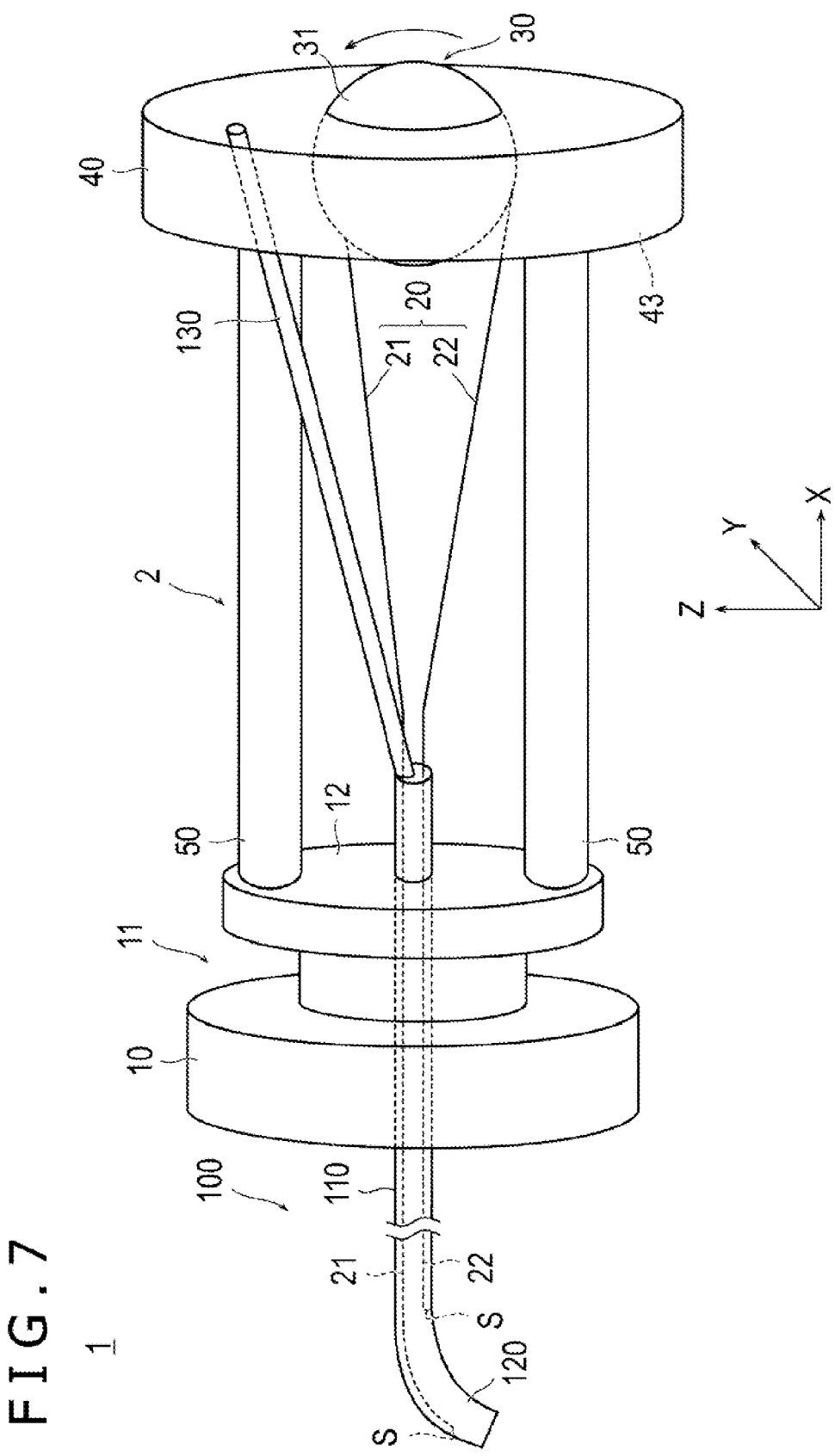
FIG. 7 is a schematic configuration diagram showing the medical instrument when the guiding catheter distal part is curved downward.

In the case of curving the guiding catheter distal part 120 in the downward Z-direction in the state of FIG. 1, the operator rotates the pull operation part 30 about the Y-axis from the lower side toward the upper side as shown in FIG. 7 by e.g. a thumb. The second wire 22 is thereby pulled toward the proximal side and thus the guiding catheter distal part 120 is curved downward.

The guiding catheter distal part 120 is curved as described above every time reaching a bifurcation of the bronchi, and thereby the guiding catheter 100 is made to reach an affected area.

As described above, according to the first embodiment, curving operation of the guiding catheter distal part 120 is enabled by carrying out rotational operation of the pull operation part 30. Thus, the curving operation of the guiding catheter 120 can be easily carried out without moving a comparatively-large member.

Furthermore, the pull operation part 30 is formed of a rotational member (main body part 31) rotatably supported by the support part 40 and pulls the pull wire 20 by a rotational action. Therefore, the guiding catheter distal part 120 is curved by carrying out rotational operation of the pull operation part 30. This enhances the operability.

In addition, the pull operation part 30 is a sphere. Therefore, the guiding catheter distal part 120 is curved by carrying out rotational operation of the sphere. This enhances the operability.

The pull operation part 30 may be a circular disc. Therefore, the guiding catheter distal part 120 is curved by carrying out rotational operation of the circular disc. This enhances the operability.

Moreover, the guiding catheter 100 is curved by rotating the pull operation part 30 to pull the pull wire 20 in a direction intersecting the axial direction of the guiding catheter 100 (X-direction). Thus, the pull wire 20 can be pulled in the direction of a tangent to the main body part 31. This suppresses separation between the pull wires 20 and the pull operation part 30, which are connected to each other at the connection points 31a and 31b.

In addition, the restricting member 32 for restricting the rotation direction of the pull operation part 30 is further provided. Therefore, the rotation direction of the pull operation part 30 is restricted, which enhances the operability.

Furthermore, the pull wires 20 have the first wire 21 and the second wire 22 fixed at positions opposed to each other in a section of the guiding catheter distal part 120 perpendicular to the axis, and the first wire 21 and the second wire 22 are each connected to the pull operation part 30. Therefore, by the rotation of the support part 40 in association with the rotation of the rotational operation part 10, the working lumen 130 rotates in association with the rotation of the guiding catheter body part 110. This allows the guiding catheter 100 to be rotated without a twist of the guiding catheter body part 110 and the working lumen 130.

<Second Embodiment>

Next, a second embodiment of the present invention will be described. Description of a part common to the first embodiment is omitted and a point that is characteristic only in the second embodiment will be described.

Figure 8:
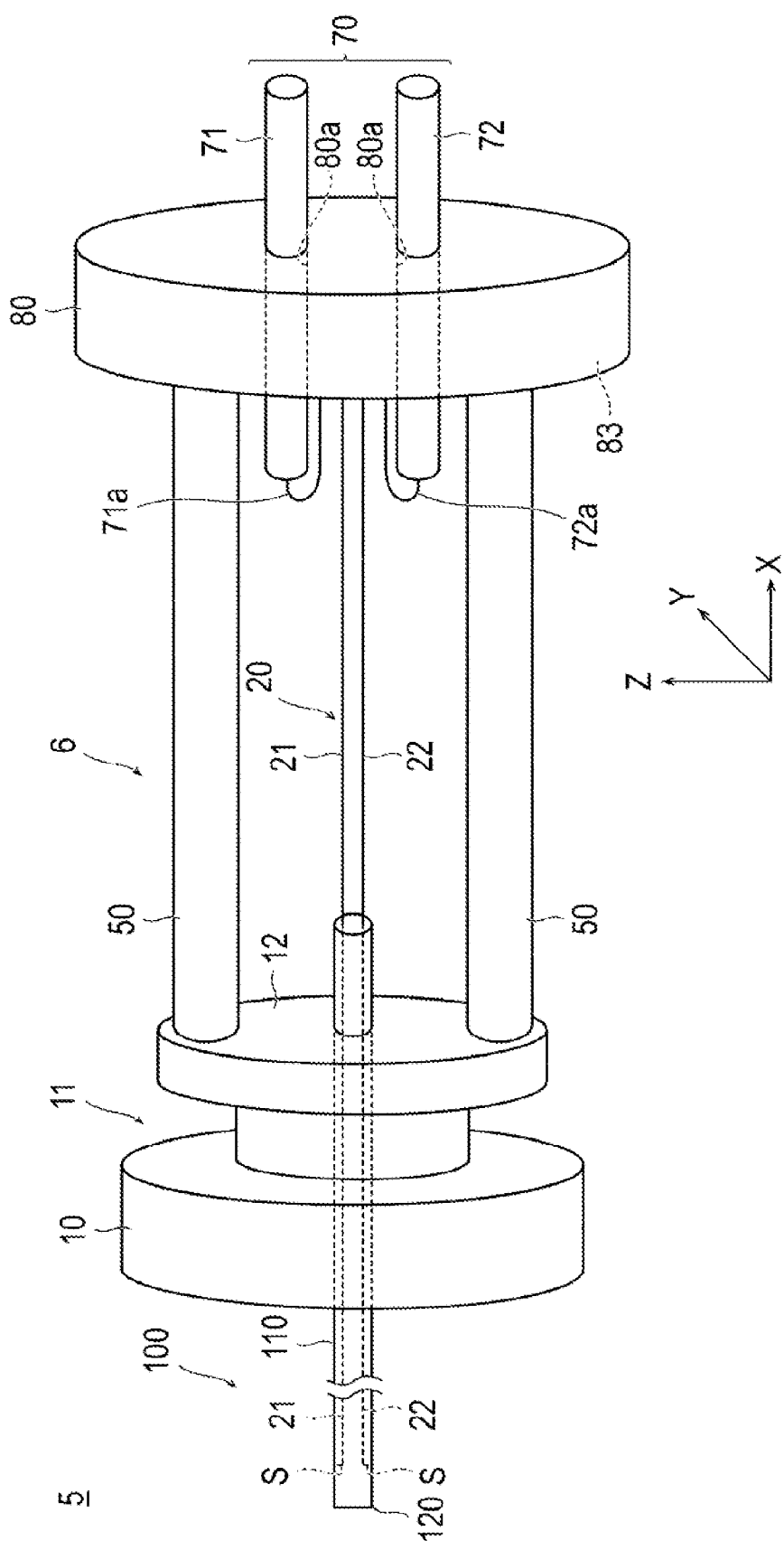
FIG. 8 is a schematic configuration diagram showing a medical instrument according to a second embodiment.
Figure 9:
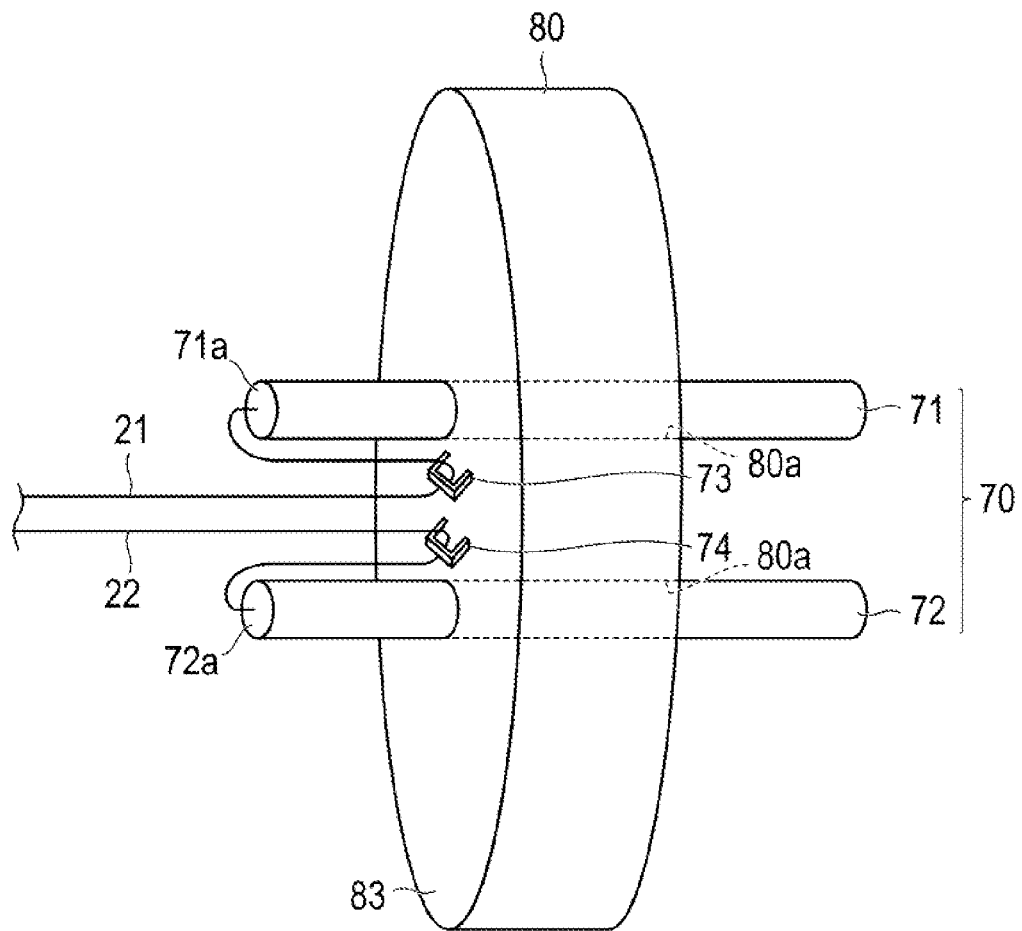
FIG. 9 is a schematic configuration diagram showing a pull operation part according to the second embodiment.

FIG. 8 is a schematic configuration diagram showing a medical instrument 5 according to the second embodiment of the present invention. FIG. 9 is a schematic configuration diagram showing a pull operation part 70 according to the second embodiment. In FIG. 8, a support protrusion and so forth are omitted for clearly showing the structure.

As shown in FIGS. 8 and 9, an operating member 6 of the medical instrument 5 according to the second embodiment of the present invention has the pull operation part 70 that is connected to the pull wires 20 and curves at least part of the guiding catheter 100 in a direction intersecting the axial direction by pulling the pull wire 20, and a support part 80 that is provided rotatably about the axis of the guiding catheter 100 and supports the pull operation part 70 in such a state that the pull action of the pull operation part 70 is possible. The other configuration is the same as the first embodiment.

The pull operation part 70 curves the guiding catheter distal part 120 by pulling the pull wire 20 in the axial direction of the guiding catheter 100. The pull operation part 70 has a first operating part 71, a second operating part 72, a first hook part 73, and a second hook part 74.

The first operating part 71 and the second operating part 72 pull the first wire 21 and the second wire 22, respectively, by a translational action. The first operating part 71 and the second operating part 72 have a circular column shape extending along the X-direction and are provided slidably in through-holes 80a of the support part 80 to be described later. The first operating part 71 and the second operating part 72 are connected to the first wire 21 and the second wire 22, respectively, at connection points 71a and 72a, respectively.

The first hook part 73 and the second hook part 74 have a gate shape and to which the first wire 21 and the second wire 22, respectively, are hooked. The first hook part 73 and the second hook part 74 are provided on a support joining surface 83 of the support part 80 to be described later in such a manner that the pull wires 20 can move through them. The first hook part 73 and the second hook part 74 may be provided with a groove, a pulley, etc. to guide pulling of the pull wires 20.

The support part 80 supports the pull operation part 70 in such a state that the translational action of the pull operation part 70 is possible. The support part 80 is a hollow member having the two through-holes 80a and has the support joining surface 83.

The two through-holes 80a are through-holes into which the first operating part 71 and the second operating part 72 are slidably inserted.

The support joining surface 83 is provided on the distal side of the support part 80 and is joined to the joining parts 50. On the support joining surface 83, the first hook part 73 and the second hook part 74 are provided.

Next, the operation of the medical instrument 5 according to the second embodiment of the present invention will be described with reference to FIGS. 10 and 11. Here, only the curving method of the guiding catheter distal part 120 will be described.

An operator causes the translational movement of the pull operation part 70 toward the distal side under radioscopy to pull the pull wire 20 in the axial direction of the guiding catheter 100 (X-direction). The operator thereby curves the guiding catheter distal part 120.

Figure 10:
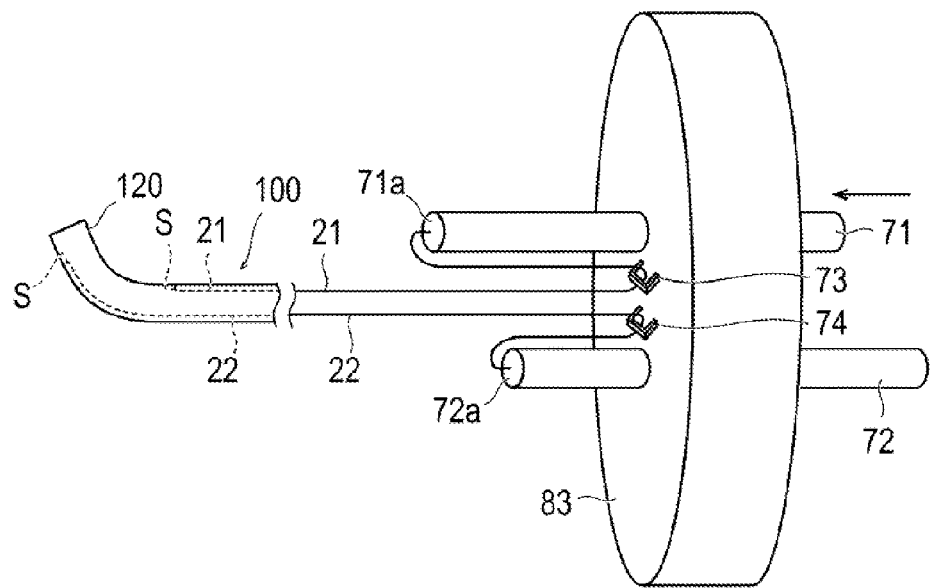
FIG. 10 is a schematic configuration diagram showing the medical instrument of the second embodiment when the guiding catheter distal part is curved upward.

Specifically, in the case of curving the guiding catheter distal part 120 in the upward Z-direction in the state of FIG. 8, the operator pushes the first operating part 71 toward the distal side as shown in FIG. 10 by e.g. a thumb. The first wire 21 at the connection point 71a thereby moves toward the distal side and the first wire 21 near the guiding catheter distal part 120 is pulled toward the proximal side via the first hook part 73. Therefore, the guiding catheter distal part 120 is curved upward.

Figure 11:
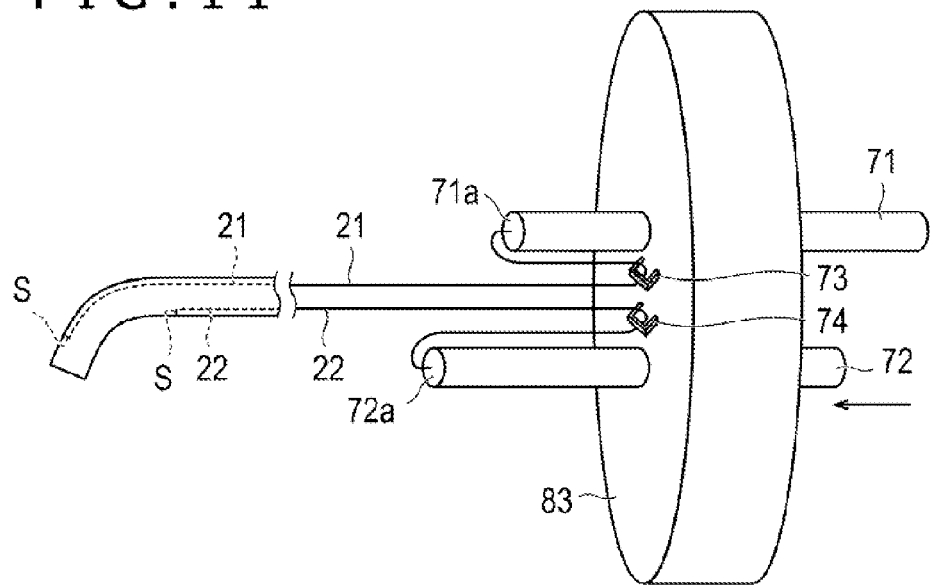
FIG. 11 is a schematic configuration diagram showing the medical instrument of the second embodiment when the guiding catheter distal part is curved downward.

In the case of curving the guiding catheter distal part 120 in the downward Z-direction in the state of FIG. 8, the operator pushes the second operating part 72 toward the distal side as shown in FIG. 11 by e.g. a thumb. The second wire 22 at the connection point 72a thereby moves toward the distal side and the second wire 22 near the guiding catheter distal part 120 is pulled toward the proximal side via the second hook part 74. Therefore, the guiding catheter distal part 120 is curved downward.

As described above, according to the second embodiment, curving operation of the guiding catheter distal part 120 is enabled by carrying out translational operation of the pull operation part 70. Thus, the curving operation of the guiding catheter 120 can be easily carried out without moving a comparatively-large member.

(Modification Examples)

Figure 12:
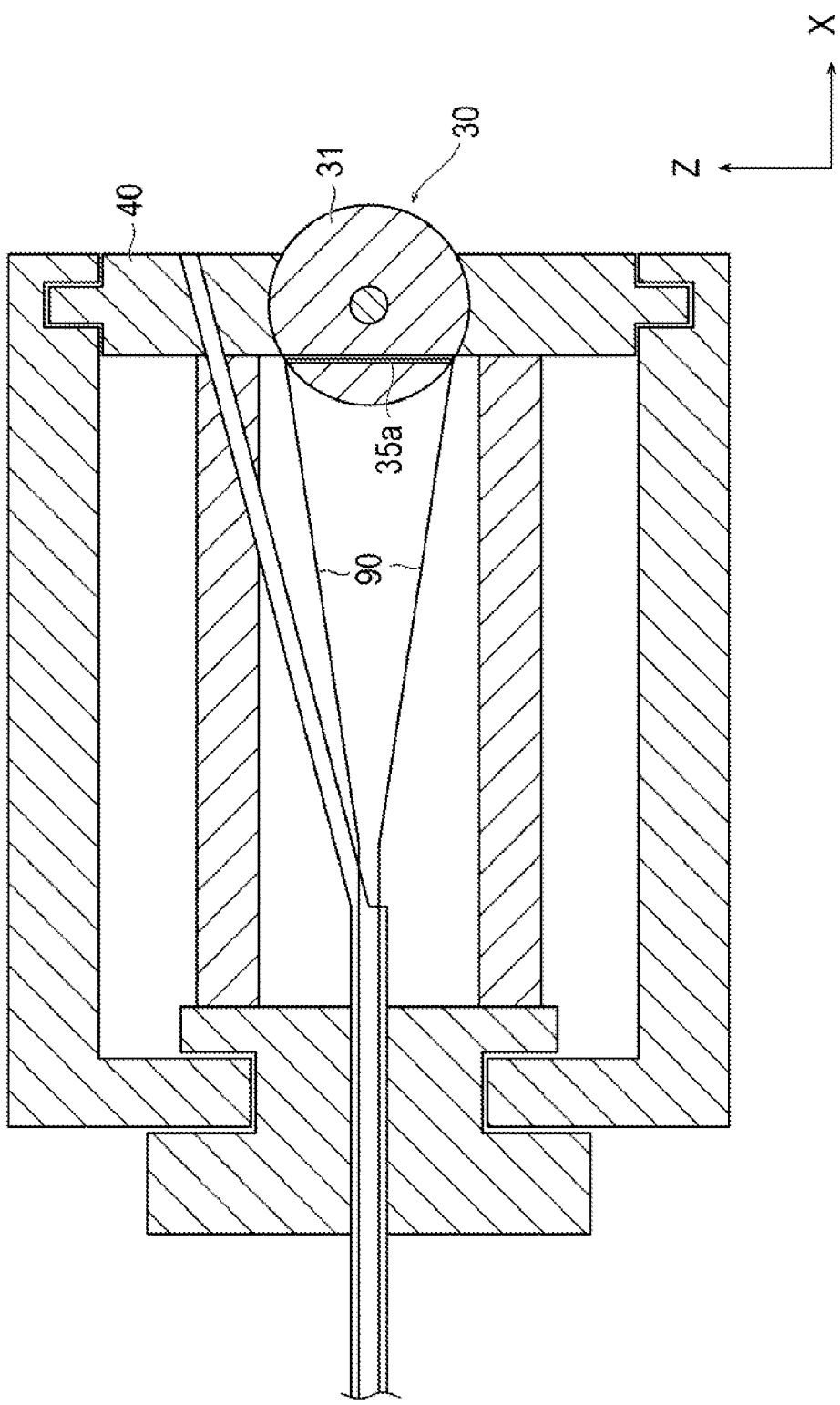
FIG. 12 is a schematic configuration diagram showing a medical instrument according to a modification example of the present invention.

In the first embodiment according to the present invention, the first wire 21 and the second wire 22 are each pulled to curve the guiding catheter distal part 120. However, the configuration is not limited thereto. As shown in FIG. 12, the guiding catheter distal part 120 may be curved by pulling one pull wire 90 inserted into a through-hole 35a made in the main body part 31 along the Z-direction by the pull operation part 30.

Figure 13:
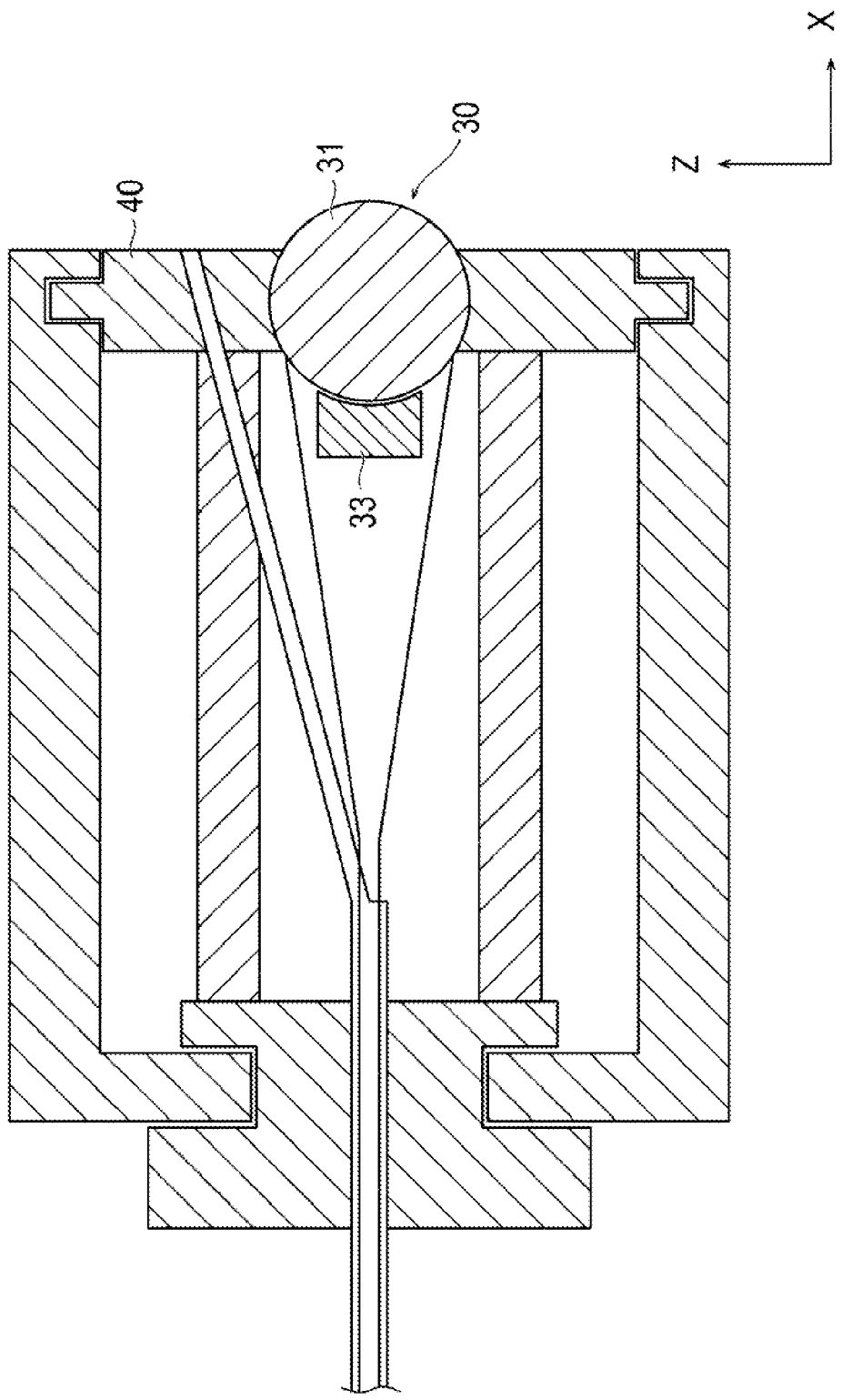
FIG. 13 is a schematic configuration diagram showing a medical instrument according to another modification example of the present invention.

Furthermore, in the first embodiment according to the present invention, the restricting member 32 is so provided as to extend along the Y-axis direction and the main body part 31 rotates about the Y-axis. However, the configuration is not limited thereto and a restricting member 33 may be provided on the distal side of the main body part 31 as shown in FIG. 13. Moreover, in this case, the number of pull wires 20 may be increased (in FIG. 13, the number of pull wires 20 is two). This enables the guiding catheter distal part 120 to be curved in three or more directions, enhancing the operability.

Figure 14:
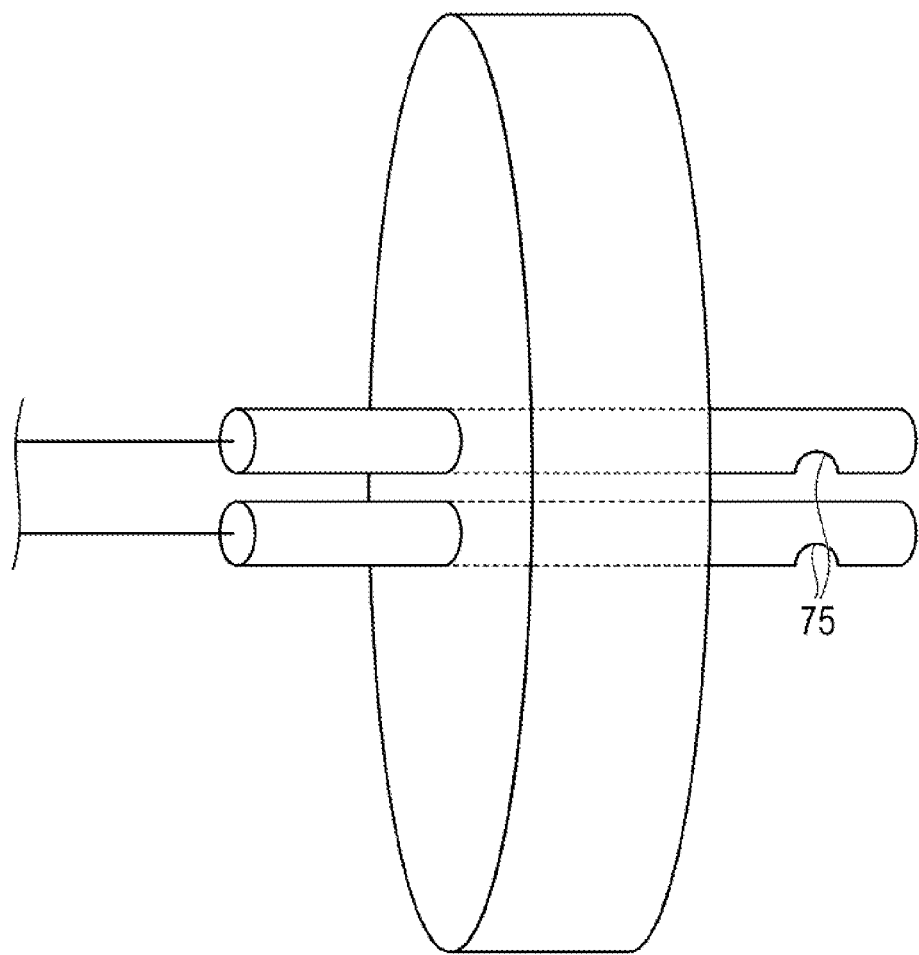
FIG. 14 is a schematic configuration diagram showing a pull operation part of a medical instrument according to further another modification example of the present invention.

In the second embodiment according to the present invention, the pull operation part 70 pulls the pull wires 20 via the first hook part 73 and the second hook part 74. However, the configuration is not limited thereto. As shown in FIG. 14, the guiding catheter distal part 120 may be curved by hooking e.g. a thumb to a thumb hooking part 75 made in the first operating part 71 and the second operating part 72 and moving the first operating part 71 and the second operating part 72 from the distal side toward the proximal side.

In the first and second embodiments according to the present invention, the operating members 2 and 6 are used as the operating member of the guiding catheter 100. However, the use purpose is not limited thereto and the operating members 2 and 6 may be used as the operating member of a catheter, a biopsy needle, forceps, a sensor, or an endoscope.

Furthermore, in the first and second embodiments according to the present invention, the operating members 2 and 6 are applied to a lung cancer biopsy. However, the application target is not limited thereto and the operating members 2 and 6 may be applied to a treatment for a lung cancer or another lung disease such as a COPD, a treatment for a stenosed part of a blood vessel, a biopsy or treatment of a digestive tract, etc.

This application is based on Japanese Patent Application No. 2012-104094 filed on Apr. 27, 2012, the disclosure of which is incorporated herein by reference in its entirety.

DESCRIPTION OF REFERENCE SYMBOLS 1, 5 Medical instrument
2, 6 Operating member
10 Rotational operation part
20, 90 Pull wire
21 First wire
22 Second wire
30, 70 Pull operation part
32, 33 Restricting member
40, 80 Support part
50 Joining part
60 Grip part
100 Guiding catheter
110 Guiding catheter body part (body part)
120 Guiding catheter distal part (distal part)
130 Working lumen

The invention claimed is:

1. An operating member for rotating an elongated body for medical use about an axis and curving at least part of the elongated body for medical use in a direction intersecting an axial direction, the operating member comprising:
    a rotational operation part that is fixed to the elongated body for medical use and rotates the elongated body for medical use about the axis;
    a pull wire fixed to the elongated body for medical use;
    a pull operation part that is connected to the pull wire and curves at least part of the elongated body for medical use in a direction intersecting the axial direction by pulling the pull wire;
    a support part that is provided rotatably about the axis of the elongated body for medical use and supports the pull operation part in such a state that a pull action of the pull operation part is possible;
    a joining part that joins the rotational operation part to the support part and rotates the support part and the pull operation part about the axis of the elongated body for medical use in association with rotation of the rotational operation part; and
    a grip part that is restricted in movement in the axial direction by being disposed between the rotational operation part and the support part and is provided pivotally independently of the rotational operation part and the support part.

2. The operating member according to claim 1, wherein the pull operation part is formed of a rotational member rotatably supported by the support part and pulls the pull wire by a rotational action.

3. The operating member according to claim 2, wherein the elongated body for medical use is curved by rotating the pull operation part to pull the pull wire in a direction intersecting the axial direction of the elongated body for medical use.

4. The operating member according to claim 2, further comprising a restricting member that restricts rotation direction of the pull operation part.

5. The operating member according to claim 1, wherein the pull operation part is a sphere.

6. The operating member according to claim 1, wherein the pull operation part is a circular disc.

7. The operating member according to claim 1, wherein
    the pull wire has a first wire and a second wire fixed at positions opposed to each other in a section of a distal part of the elongated body for medical use perpendicular to the axis, and
    the first wire and the second wire are each connected to the pull operation part.

8. A medical instrument comprising:
    the operating member according to claim 1; and
    the elongated body for medical use including a body part fixed to the rotational operation part, a distal part curved by the pull operation part, and a working lumen extending from the body part to the support part.

* * * * *